US010329306B2

(12) United States Patent
Zhao (10) Patent No.: US 10,329,306 B2
(45) Date of Patent: Jun. 25, 2019

(54) CRYSTALLINE FORM OF 1-(1-METHYL-1H-PYRAZOL-4-YL)-N-((1R,-5S,7S)-9-METHYL-3-OXA-9-AZABICYCLO-[3.3.1]NONAN-7-YL)-1H-INDOLE-3-CARBOXAMIDE (71) Applicant: Takeda Pharmaceutical Company Limited, Osaka (JP)

(72) Inventor: Yuxin Zhao, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/515,263

(22) PCT Filed: Sep. 29, 2015

(86) PCT No.: PCT/US2015/052806
§ 371 (c)(1),
(2) Date: Mar. 29, 2017

(87) PCT Pub. No.: WO2016/053947
PCT Pub. Date: Apr. 7, 2016

(65) Prior Publication Data
US 2017/0233406 A1  Aug. 17, 2017

Related U.S. Application Data (60) Provisional application No. 62/056,982, filed on Sep. 29, 2014.

(51) Int. Cl.
*C07D 498/08* (2006.01)

(52) U.S. Cl.
CPC ........ *C07D 498/08* (2013.01); *C07B 2200/13* (2013.01)

(58) Field of Classification Search
CPC .................................................. C07D 498/08
See application file for complete search history.

(56) References Cited

U.S. PATENT DOCUMENTS

| 4,107,288 | A | 8/1978 | Oppenheim et al. |
| 4,789,673 | A | 12/1988 | Donatsch et al. |
| 4,789,763 | A | 12/1988 | Nagata et al. |
| 4,803,199 | A | 2/1989 | Donatsch et al. |
| 4,886,808 | A | 12/1989 | King |
| 4,910,193 | A | 3/1990 | Buchheit |
| 5,034,398 | A | 7/1991 | King |
| 5,145,684 | A | 9/1992 | Liversidge et al. |
| 5,298,510 | A | 3/1994 | Tyers |
| 5,334,831 | A | 8/1994 | Maurice |
| 7,538,114 | B2 | 5/2009 | Hitchcock et al. |
| 9,012,447 | B2 | 4/2015 | Hitchcock et al. |
| 9,346,829 | B2 | 5/2016 | Hitchcock et al. |
| 9,670,229 | B2 | 6/2017 | Hitchcock et al. |
| 2004/0038958 | A1 | 2/2004 | Rundfeldt et al. |
| 2005/0234095 | A1 | 10/2005 | Xie et al. |
| 2007/0191313 | A1 | 8/2007 | Beard et al. |
| 2011/0319407 | A1 | 12/2011 | Xie et al. |

FOREIGN PATENT DOCUMENTS

| CN | 100353946 C | 3/2006 |
| CN | 101001856 | 7/2007 |
| CN | 101778850 | 7/2010 |
| CN | 102046176 C | 5/2011 |
| EP | 0200444 | 11/1986 |
| EP | 0351385 | 1/1990 |
| EP | 0377967 | 7/1990 |
| EP | 0469449 | 2/1992 |
| EP | 0491664 | 6/1992 |
| EP | 0558923 | 9/1993 |
| EP | 0708105 | 4/1996 |
| EP | 1156045 | 11/2001 |
| EP | 1243268 | 9/2002 |
| JP | S61-275276 | 12/1986 |
| JP | H04-021681 | 12/1992 |
| JP | H05-310749 | 11/1993 |
| JP | H08-169889 | 7/1996 |
| JP | 5816400 | 8/2005 |
| JP | 2007-530590 | 11/2007 |
| JP | 2010-535816 | 11/2010 |
| JP | 2015/522619 | 8/2015 |
| JP | 5778877 | 9/2015 |
| JP | 6275675 | 3/2016 |
| WO | 94/03452 | 2/1994 |
| WO | 1995/027490 | 10/1995 |
| WO | 96/12722 | 5/1996 |
| WO | 2003/035625 | 5/2003 |
| WO | 2004/006920 | 1/2004 |
| WO | 2004/029050 | 4/2004 |
| WO | 2004062623 | 7/2004 |
| WO | 2004/089470 | 10/2004 |
| WO | 2005092890 | 10/2005 |
| WO | 2006/077365 | 7/2006 |
| WO | 2007/038367 | 4/2007 |
| WO | 2007/095561 | 8/2007 |

(Continued)

OTHER PUBLICATIONS

International Search Report, dated Nov. 27, 2015, for PCT Application No. PCT/US2015/052806, filed Sep. 29, 2015.
Written Opinion of the International Searching Authority, dated Nov. 27, 2015 for PCT Application No. PCT/US2015/052806, filed Sep. 29, 2015.
International Preliminary Report on Patentability, dated Nov. 27, 2015, for PCT Application No. PCT/US2015/052806, filed Sep. 29, 2015.
Notification of the First Chinese Office Action, dated Sep. 3, 2018 in Chinese Application No. 201580052611.3.
Weng Lingling, Clinical Pharmaceutical Chemistry, 2007, pp. 346-348.
Caira, M., Crystalline Polymorphism of Organic Compounds, Department of Chemistry, University of Cape Town, Rondebosch 7700, South Africa, pp. 164-208.

(Continued)

*Primary Examiner* — Paul V Ward
(74) *Attorney, Agent, or Firm* — Barnes & Thornburg LLP; Scott Rothenberger (57) ABSTRACT

Disclosed is a crystalline polymorph 1-(1-methyl-1H-pyrazol-4-yl)-N-((1R,5S,7S)-9-methyl-3-oxa-9-azabicyclo [3.3.1]nonan-7-yl)-1H-indole-3-carboxamide, Form G, and processes for making the same.

6 Claims, 1 Drawing Sheet

(56) References Cited

FOREIGN PATENT DOCUMENTS

| WO | 2008/048981 | 4/2008 |
|---|---|---|
| WO | 2008/097930 | 8/2008 |
| WO | 2008/100867 | 8/2008 |
| WO | 2009/023623 | 2/2009 |
| WO | 2009/108551 | 9/2009 |
| WO | 2009155054 | 12/2009 |
| WO | 2011/126821 | 10/2011 |
| WO | 2011/153553 | 12/2011 |
| WO | 2014/014951 | 1/2014 |
| WO | 2014014962 | 1/2014 |
| WO | WO2014014951 | * 1/2014 |

OTHER PUBLICATIONS

Hewlett et al., "Pilot Trial of Ondansetron in the Treatment of 8 Patients with Obsesive-Compulsive Disorder", 2003 Journal of Clinical Psychiatry 64:9, Sep. 2003, pp. 1025-1030.
Kelley et al., "Targeted gene deletion of the 5-HT3 receptor subunit produces an anxiolytic phenotype in mice", 2003, European Journal of Pharmacology. 461, (2003), pp. 19-25.
Haus et al., "Oral treatment of fibromyalgia with tropisetron given over 28 days: influence on functional and vegetative symptoms, psychometric parameters and pain", Scand J. Rhematol 2000: 29 Suppl. 113, pp. 55-58.
Farris et al., "Evidence for a vagan pathophysiology for bulimia nervosa and the accompanying depressive symptoms", Journal of Affective Disorders 92 (2006), pp. 79-90.
Hammer et al., "Serotonin3 receptor antagonists block anorectic responses to amino acid imbalance", American Physiology Society 1990, R627-R636.
Jiang et al., "Anorectic Response of Amino Acid Imbalance: A Selective Serotinin3 Effect?" Pharmacology Biochemistry and Behavior, 1994, vol. 47, pp. 59-63.
Hermann et al., "Functional Antagonistic Properties of Clozipine at the 5-HT3 Receptor", Biochemical and Biophysical Research Communications (1996) 225, pp. 957-960.
Sirota et al., "Use of the Selective Serotonin 3 Receptor Antagonist Ondansetron in the Treatment of Neuroleptic-Induced Tardive Dyskinesia", American Journal Psychiatry, 2000; 157: pp. 287-289.
Adler et al., "Improved P50 Auditory Gating with Ondansetron in Medicated Schizophrenia Patients", American Journal of Psychiatry 2005: 162, pp. 386-388.
Koike et al., "Tropisetron improves deficits in auditory P50 suppression in schizophrenia", Schizophrenia Research 76 (2005), pp. 62-72.
Zhang et al., "Beneficial effects of ondansetron as an adjunct to haloperidal for chronic, treatment-resistant schizophrenia: A double-blind, randomized, placebo-controlled study", Schizophrenia Research, 2006: 88, pp. 102-110.
Akhonzadeh et al, "Added ondansetron for stable schizophrenia: A double blind, placebo", Schizophrenia Research, 107, (2009), pp. 206-212.
Costall et al., "5-HT3 Receptors" Current Drug Targets—CNS Neurological Disorders, 2004, 3, pp. 27-37.
Johnson et al., "Ondansetron reduces the craving of biologically predisposed alcoholics", Psychopharmacology Feb. 12, 2002, 160, pp. 408-413.
Johnson et al., "Role of the serotonergic System in the Neurobiology of Alcoholism", Implications for Treatment, CNS Drugs, 2004: 18:(15), pp. 1105-1118.
Kayser et al, Mechanical, thermal and formalin-induced nociception is differentially altered in 5-HT1A-/-, 5-HT1B-/-, 5-HT2A-/-, 5-HT3A-/- and 5-HTT-/- knock-out male mice, International Association for the Study of Pain, (2007), 130, pp. 235-248.
Glaum et al., "Reversal of the antinociceptive effects of intrathecally administered serotonin in the rat by a selective t-HT3 receptor antagonist", 1998 Neuroscience Letters, (1988), pp. 313-317.

Schworer et al., "Treatment of pruritus: a new indication for serotonin type 3 receptor antagonists", Clinical Investigator, 1993, 71, pp. 659-662.
Thompson et al., "The 5-HT3 receptor as a therapeutic target", 2007 Expert Opinion, Therapeutic Targets, (2007), 11(4), pp. 527-540.
Graeff, "Serotonergic Systems", Psychiatric Clinics of North America, vol. 2, No. 4, Dec. 1997, pp. 723-739.
Barnes et al., "The 5-HT3 receptor—the relationship between structure and function", Neuropharmacology 56 (2009), pp. 273-284.
Fiebich et al., "Expression of 5-HT3A receptors in cells of the immune system", 2004 Scandinavian Journal of Rheumatology, (2004), 33, pp. 9-11.
Stratz et al., Identification of t-HT3 receptors on human platelets: Increased surface immunoreactivity after activation with adenosine diphosphate (ADP) and thrombin receptor-activating peptide (TRAP), 2008 Thromb Haemost 99; pp. 784-786.
Hoff et al., "Quantitative Assessment of Glial Cells in the Human and Guinea Pig Enteric Nervous System With an Anti-Sox8/9/10 Antibody", Journal of Comparative Neurology, 2008, 509, pp. 356-371.
Kapeller et al., "Serotonin receptor diversity in the human colon: Expression of serotonin type 3 receptor subunits 5-HT3C, 5-HT3D, and 5-HT3E", Journal of Comparative Neurology, Feb. 15, 2011, 519(3), pp. 420-432.
First Office Action for Chinese Application No. 201580052611.3 dated Sep. 3, 2018 and its English translation.
Chinese Office Action for Chinese Application No. 201610902465.5, dated Dec. 1, 2017 and English Translation.
Second Office Action for Chinese Application No. 201610902465.5 dated Jun. 8, 2018 and its English Translation.
Third Office Action for Chinese Application No. 201610902465.5 dated Jun. 8, 2018 and its English Translation.
Substantive examination Report for Dominican Republic Application No. P2015-0009 dated Jul. 6, 2018 and its English Translation.
Examination Report for Indian Application No. 957/DELNP/2015 dated Aug. 24, 2018.
Search Report with Written Opinion for Moroccan Application No. PV/37836 and its English Translation.
Indonesia office Action for Indonesia Application No. P-00201500890 dated Jun. 21, 2018 and its English Translation.
English Translation of Mexican Office Action for Mexican Application No. MX/a/2015/000783.
Thailand Office Action for Thailand Application No. 1501000246 dated Jul. 12, 2017 and its English Translation.
Israel Office Action for Israel Application No. 236702 dated Aug. 21, 2017 and English translation.
English translation of Vietnam Office Action for Vietnam Application No. 1-2015-0057 dated Sep. 26, 2017.
Extended European Search Report for European Application No. 17198245.7 dated Jan. 30, 2018.
International Search Report for PCT/US2013/050746.
Written Opinion for PCT/US2013/050746.
IPRP for PCT/US2013/050746.
Exam Report for European Application No. 13742355.4 dated Mar. 22, 2016.
Restriction Requirement for U.S. Appl. No. 13/943,634 dated Jul. 8, 2014.
Office Action for U.S. Appl. No. 13/943,634 dated Sep. 16, 2014.
Restriction Requirement for U.S. Appl. No. 14/645,639 dated Oct. 9, 2015.
Office Action for U.S. Appl. No. 15/150,013 dated Sep. 15, 2016.
Office Action for U.S. Appl. No. 15/599,239 dated Aug. 28, 2017.
Ex Parte Quayle Action for U.S. Appl. No. 15/599,239 dated Feb. 2, 2018.
Restriction Requrirement for U.S. Appl. No. 16/041,875 dated Sep. 5, 2018.
First Office Action for Chinese Application 201380045326.X and its English translation.
Exam report for Japanese patent application No. 523192/2015 dated Jun. 17, 2015 and its English translation.
Search Report for Japanese Application 189035/2015 and its English translation.

(56) References Cited

OTHER PUBLICATIONS

Exam Report for Japanese Application No. 189035/2015 dated Mar. 2, 2017 and its English translation.
Exam Report for Japanese Application 189035/2015 dated Aug. 22, 2017 and its English Translation.
Exam Report for Japanese Application No. 223856/2017 dated Nov. 6, 2018 and its English translation.
Ciara, "Crystalline Polymorphism of Organic Compounds", Topics in Organic Chemistry, vol. 198, 1998, p. 163-208.
Dawes et al., "Reductions in and relations between "craving" and drinking in a prospective, open-label trial of ondansetron in adolescents with alcohol dependence", Addictive Behaviors 30, (2005), 1630-1637.
Johnson, et al, "A preliminary randomized, double-blind, placebo-controlled study of the safety and efficacy of ondansetron in the treatment of cocaine dependence", Drug and Alcohol Dependence, (2006), 84, 256-263.
Davies et al, A Novel Class of Ligand-gated Ion Channel is Actviated by Zn2+, The Journal of Biological Chemistry, vol. 278, Issue of Jan. 10, 2003, pp. 712-717.
Connolly et al, "The Cys-loop superfamily of ligand-gated ion channels: the impact of receptor structure on function", Biochemical Society, Transaction (2004) vol. 32, 529-534.
Boess et al., 1995, "Ultrastructure of the 5-Hydroxytryptamine3 Receptor", Journal of Neurochemistry, (1995), 64, 1401-1405.
Anderson et al, "Examination of Association of Genes in the Serotonin System to Autism", Neurogentics, 2009, 10(3), 209-216.
King et al, "Substituted Bezamides with Conformationally Restricted Side Chains, 5. Azabicyclo[x,y,z] Derivatives as 5-HT4 Receptor Agonists and Gastric Motility Stimulants", Journal of Medicinal Chemistry, 1993, 36, 683-689.
Papke, et al, "Activation and Desensitization of Nicotinic a7-type Acetylcholine Receptors by Benzylidene Anabaseines and Nicotine", Journal of Pharmacololgy and Experimental Therapeutics, 2009, 329(2), pp. 791-807.
Boess et al, Pharmacological and behavioral profile of N-[(3R)-1-azabicyclo[2.2.2]oct3-yl]-6-chinolincarboxamide (EVP-5141), a novel a7 nicotinic acetycholine receptor agonist/serotonin 5-HT3 receptor antagonist:, Psychopharmocology, 2013, 227, pp. 1-17.
Naghdi et al, "The effect of intrahippocampal injectioins of ritanserin (5HT2A/2C antagonist) and granisetron (5HT3 antagonist) on learning as assessed in the spatial version of the water maze", Behavioral Brain Research 157, 2005, pp. 205-210.
Javadi-Paydar et al., "Involvement of nitric oxide in granisetron improving effect on scopolamine-induced memory impairment in mice", Brain Research, 1429, (2012) p. 61-71.

\* cited by examiner

2-Theta (degrees)

CRYSTALLINE FORM OF 1-(1-METHYL-1H-PYRAZOL-4-YL)-N-((1R,5S,7S)-9-METHYL-3-OXA-9-AZABICYCLO-[3.3.1]NONAN-7-YL)-1H-INDOLE-3-CARBOXAMIDE

FIELD OF THE INVENTION

The present invention relates generally to a certain polymorphic form and pharmaceutical science.

BACKGROUND OF THE INVENTION

Polymorphism relates to the occurrence of different crystal forms for a molecule. These different crystalline forms have distinct crystal structures and vary in physical properties like melting point and XRPD spectrum. A particular polymorph may have advantageous properties for the manufacture and use of the drug substance.

The present invention relates to a particular polymorphic form of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, free base, which is an antagonist of the 5-HT3 receptor. 1-(1-Methyl-1H-pyrazol-4-yl)-N-((1R,5S,7S)-9-methyl-3-oxa-9-azabicyclo[3.3.1]nonan-7-yl)-1H-indole-3-carboxamide, 2,2,2-trifluoroacetic acid salt, is disclosed in PCT Publication No. WO 2014/014951, published Jan. 23, 2014.

The present polymorphic form, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, provides an anhydrate form, that can be readily and reproducibly produced and is stable to prolonged thermal stress.

SUMMARY OF THE INVENTION

The present invention provides a novel polymorph of 1-(1-methyl-1H-pyrazol-4-yl)-N-((1R,5S,7S)-9-methyl-3-oxa-9-azabicyclo[3.3.1]nonan-7-yl)-1H-indole-3-carboxamide. More specifically, the present invention provides 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G.

The present invention also provides a pharmaceutical composition comprising 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, and a pharmaceutically acceptable excipient.

The present invention also provides a methods of treating a disease treatable by administration of a 5-HT3 receptor antagonist which method comprises administrating to the patient 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G. That is, the present invention provides a method of treating a disease treatable by administration of a 5-HT3 receptor antagonist comprising: administrating to a patient in need thereof a therapeutically effective amount of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G. The invention is directed to the use of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, to treat a disease treatable by administration of a 5-HT3 receptor antagonist as disclosed herein, that is, the use of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, for the manufacture of a medicament to treat diseases treatable by administration of a 5-HT3 receptor antagonist as disclosed herein.

DETAILED DESCRIPTION OF THE INVENTION

As used herein terms have their using conventional abbreviations, unless otherwise indicated, for example: methanol (MeOH), ethanol (EtOH), isopropanol (IPA), n-butanol (n-BuOH), acetonitrile (MeCN), tetrahydrofuran (THF), 2-methyl tetrahydrofuran (2-MeTHF), MeOAc (methyl acetate), ethyl acetate (EtOAc), isopropyl acetate (IPAc), methyl ethyl ketone (MEK), methylisobutyl ketone (MIBK), dichloromethane (DCM), dimethyl sulfoxide (DMSO), dimethylamide (DMF), and N-methyl-2-pyrrolidone (NMP).

As used herein, the term "$C_{2-4}$ alkylnitrile" refers to a straight or branched alkyl chain having a nitrile, and having a total of from two to four carbon atoms, for example acetonitrile and propionitrile.

The term "$C_{3-7}$ alkylacetate" refers to straight or branched alkyl esters of acetic acid having a total of three to seven carbons, for example, ethyl acetate, isopropyl acetate, and the like.

The term "$C_{1-6}$ alcohol" a straight or branched alcohols having from one to six carbon atoms, for example methanol, ethanol, n-propanol, iso-propanol, 1,3-propanediol, and the like.

The term "$C_{2-8}$ ether" refers to a straight, branched, or cyclic alkyl ethers having a total of from two to eight carbon atoms, for example diethyl ether, methyl-t-butyl ether, THF, dioxane, and the like.

The term "$C_{6-9}$ aromatic hydrocarbons" refers to benzene and alkyl substituted benzene, such a toluene, xylene, and the like.

The term "$C_{3-5}$ N,N-dimethylcarboxamides" refers to N,N-dimethylamides of a $C_{1-3}$ carboxylic acid, for example N,N-dimethylformamide.

The term "$C_{3-7}$ alkanones" refers to a straight or branched alkyl chain having an oxo group and having a total of from three to seven carbon atoms, for example acetone and methyl ethyl ketone.

It is understood that the terms "crystallize," "crystallizing," and "crystallization" include complete dissolution followed by precipitation and slurry processes that do not involve complete dissolution.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. The term "pharmaceutically acceptable excipient" as used in the specification and claims includes both one and more than one such excipient. Pharmaceutically acceptable excipients are well known in the art, such as those in Remington's Pharmaceutical Sciences, 17th ed., Mack Publishing Company, Easton, Pa., 1985.

The terms "condition," "disorder," and "disease" relate to any unhealthy or abnormal state.

"Treat," "treating," or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting, controlling, slowing, stopping, or reducing the development of the disease or its clinical symptoms; or (3) relieving the disease, i.e., causing regression of the disease or its clinical symptoms or improvement of the disease or its clinical symptoms. The terms "treat," "treating," and "treatment," do not necessarily indicate a total elimination of any or all symptoms or a cure of the disease.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

The term "substantially pure" refers to greater than 90%, preferably greater than 97%, and more preferably greater than 99% polymorphic purity.

A "therapeutically effective amount" means the amount of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, that when administered in single or multiple doses, to a mammal for treating a disease, is sufficient to effect such treatment for the disease. The "therapeutically effective amount" can vary depending on the disease and its severity; the age, weight, etc., of the mammal to be treated; the degree of or involvement or the severity of the condition, disorder, or disease; the response of the individual patient; the mode of administration; the bioavailability characteristics of the preparation administered; the dose regimen selected; the use of concomitant medication; and other relevant circumstances.

The term "disease treatable by administration of a 5-HT3 receptor antagonist" includes emesis, migraine, substance abuse and addiction, neurodegenerative and psychiatric disorders such as anxiety and depression, eating disorders, schizophrenia, cognitive dysfunction associated with schizophrenia, Parkinson's disease, Huntington's Chorea, presenile dementias and Alzheimer's disease, and pain; GI disorders such as dyspepsia, gastroesophagal reflux disease, and irritable bowel syndrome; and immunological disorders and inflammation such as atherosclerosis, tendomyopathies and fibromyalgia. In a particular embodiment the disease is cognitive dysfunction associated with schizophrenia also known as cognitive impairment associated with schizophrenia.

Figure 1:
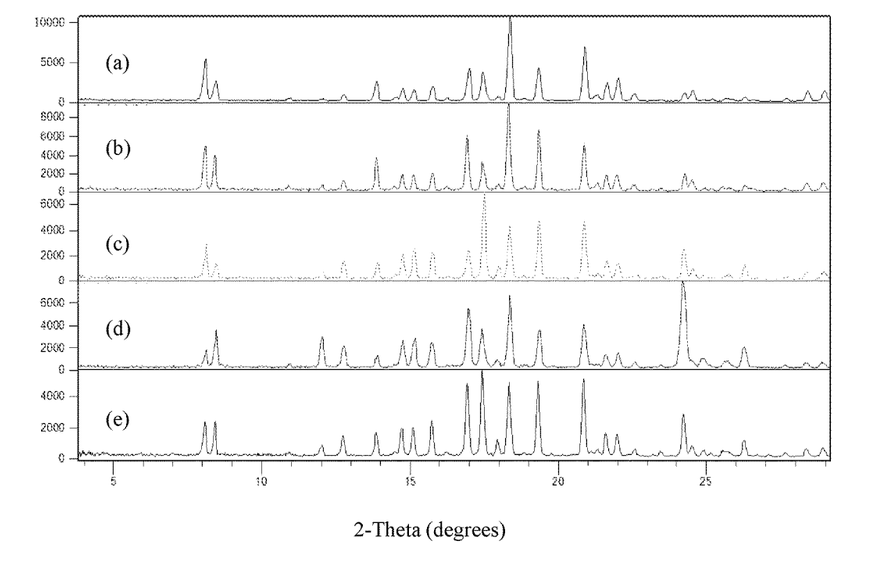
The drawing shows X-ray powder diffraction patterns (counts vs. degrees 2-theta) of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, which was prepared from a hydrate of 1-(1-methyl-1H-pyrazol-4-yl)-N-((1R,5S,7S)-9-methyl-3-oxa-9-azabicyclo[3.3.1]nonan-7-yl)-1H-indole-3-carboxamide using different solvents and/or conditions for crystallization: (a) starting material heated to 50° C. in DMSO, followed by aqueous NaOH (4 M); mixture stirred at 50° C. for 30 minutes and then allowed to cool to room temperature over a 4-hour period; (b) starting material heated to 70° C. in MeCN, followed by addition of H$_2$O at 70° C.; mixture placed in a refrigerator at 4° C. for 16 hours; (c) starting material heated to 70° C. in DMSO, followed by addition of H$_2$O at 70° C.; mixture placed in a refrigerator at 4° C. for 16 hours; (d) starting material heated to 70° C. in NMP, followed by addition of H$_2$O at 70° C.; mixture placed in a refrigerator at 4° C. for 16 hours; (e) starting material heated to 70° C. in DMSO, followed by addition of H$_2$O at 70° C.; mixture cooled at 20° C./hour to room temperature and allowed to equilibrate at room temperature over a 16-hour period.

1-(1-Methyl-1H-pyrazol-4-yl)-N-((1R,5S,7S)-9-methyl-3-oxa-9-azabicyclo[3.3.1]nonan-7-yl)-1H-indole-3-carboxamide, Form G, can be characterized by X-ray powder diffraction. See the drawing. The peaks were measured using a powder diffractometer equipped with a copper X-ray source, primary beam monochromator, and position sensitive detector. The incident beam was collimated using a 1° divergence slit. The Cu KV source was operated at 45 kV and 40 mA. X-ray powder diffraction data were collected from 3 degrees to 45 degrees in a step width of 0.02 degrees and a time per step of 10 seconds. The diffractometer was well calibrated with a silicon standard. A typical precision of the 2-theta values is in the range of about ±0.2 degrees 2-theta. Thus an X-ray diffraction peak that appears at 8.13 degrees 2-theta can appear between 7.93 and 8.33 degrees 2-theta on typical X-ray diffractometers under standard conditions.

1-(1-Methyl-1H-pyrazol-4-yl)-N-((1R,5S,7S)-9-methyl-3-oxa-9-azabicyclo[3.3.1]nonan-7-yl)-1H-indole-3-carboxamide, Form G, was found to have the following peaks, among others, rounded to 2 significant figures: 8.13, 17.01, 17.49, 18.39, and 20.91 degrees 2-theta, each ±0.2 degrees 2-theta. Form G of 1-(1-methyl-1H-pyrazol-4-yl)-N-((1R,5S,7S)-9-methyl-3-oxa-9-azabicyclo[3.3.1]nonan-7-yl)-1H-indole-3-carboxamide may be characterized by X-ray diffraction peaks at 8.13 and 18.39 degrees 2-theta, each ±0.2 degrees 2-theta. Thus, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be characterized by peaks at 8.13, 17.01, and 18.39 degrees 2-theta, each ±0.2 degrees 2-theta; by peaks at 8.13, 17.49, and 18.39 degrees 2-theta, each ±0.2 degrees 2-theta; and by peaks at 8.13, 18.39, and 20.91 degrees 2-theta, each ±0.2 degrees 2-theta.

In addition, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be characterized by peaks at 8.13, 17.01, 17.49, and 18.39 degrees 2-theta, each ±0.2 degrees 2-theta; by peaks at 8.13, 17.01, 18.39, and 20.91 degrees 2-theta, each ±0.2 degrees 2-theta; and by peaks at 8.13, 17.49, 18.39, and 20.91 degrees 2-theta, each ±0.2 degrees 2-theta. 1-(1-Methyl-1H-pyrazol-4-yl)-N-((1R,5S,7S)-9-methyl-3-oxa-9-azabicyclo[3.3.1]nonan-7-yl)-1H-indole-3-carboxamide, Form G, may also be characterized by peaks at 8.13, 17.01, 17.49, 18.39, and 20.91 degrees 2-theta, each ±0.2 degrees 2-theta.

It is recognized that the relative intensity of X-ray diffraction peaks can be dependent on preferred orientation and other factors. Although the position of the peak along the 2-theta axis does not change with preferred orientation, the intensity of the peak may change. See, for example, the drawing. Therefore, a sample of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may require processing to mitigate such factors, such as grinding the sample in an agate mortar and pestle or other measures.

Form G of 1-(1-methyl-1H-pyrazol-4-yl)-N-((1R,5S,7S)-9-methyl-3-oxa-9-azabicyclo[3.3.1]nonan-7-yl)-1H-indole-3-carboxamide may also be characterized by differential scanning calorimetry. A thermogram of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, provides a single endothermic event at about 214.5° C., which is consistent with a melt. Thermal gravimetric analysis of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, showed no weight loss prior to the melt.

The present invention also provides a process for making 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, comprising crystallizing 1-(1-methyl-1H-pyrazol-4-yl)-N-((1R,5S,7S)-9-methyl-3-oxa-9-azabicyclo[3.3.1]nonan-7-yl)-1H-indole-3-carboxamide.

The crystallization of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, is generally carried out in a solvent or combination of solvents. Suitable solvents may include DMSO, NMP, $C_{2-4}$ alkylnitrile, $C_{3-7}$ alkylacetate, $C_{1-6}$ alcohol, $C_{2-8}$ ether, $C_{3-7}$ alkanone, $C_{6-9}$ aromatic hydrocarbons, and $C_{3-5}$ N, N-dimethylcarboxamide. The crystallization of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, is beneficially carried out using an anti-solvent.

Thus, the selected solvent may contain anti-solvents, that is, a solvent or solvents in which the compound is less soluble than in the selected solvent. Generally, an anti-solvent should be miscible in the selected solvent(s). For example, water may be an anti-solvent for DMSO, NMP, and $C_{1-6}$ alcohol; $C_{2-8}$ ether, in particular MTBE, may be an anti-solvent for $C_{2-4}$ alkylnitrile, $C_{3-7}$ alkylacetate, $C_{1-6}$ alcohol, $C_{2-8}$ ether, such as THF or 2-MeTHF, $C_{3-7}$ alkanone, and $C_{6-9}$ aromatic hydrocarbons; and n-heptane may be an anti-solvent for $C_{3-7}$ alkylacetate, $C_{1-6}$ alcohol, $C_{2-8}$ ether, and $C_{3-7}$ alkanone.

Specific solvent/anti-solvent combinations may include the following: MeOH/water, IPA/water, DMSO/water, NMP/water, MeOH/MTBE, EtOH/MTBE, IPA/MTBE, n-BuOH/MTBE, MeCN/MTBE, THF/MTBE, 2-MeTHF/MTBE, MeOAc/MTBE, EtOAc/MTBE, IPAc/MTBE, acetone/MTBE, MEK/MTBE, MIBK/MTBE, DMSO/MTBE, DMF/MTBE, NMP/MTBE, MeOH/n-heptane, EtOH/n-heptane, IPA/n-heptane, n-BuOH/n-heptane, MeCN/n-heptane, THF/n-heptane, 2-MeTHF/n-heptane, MeOAc/n-heptane, EtOAc/n-heptane, IPAc/n-heptane, acetone/n-heptane, MEK/n-heptane, MIBK/n-heptane, DMSO/n-heptane, DMF/n-heptane, and NMP/n-heptane.

For example, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, is crystallized from a solvent. The temperature can range from about 30° C. to up to the reflux temperature of the selected solvent and is usually less than 115° C. The solvent should be one in which 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, is somewhat soluble. The volume of solvent is not critical but is typically minimized as a matter of convenience. An anti-solvent may be added to the heated solvent or as the mixture cools. Where the crystallization involves complete dissolution, the rate of cooling is not critical; however, slow cooling is preferred (e.g., cooling at a rate of about 20° C./hour to ambient temperature and then allowed to equilibrate at ambient temperature for about 16 hours). Slurry processing may be used. Optionally, the crystallization may be seeded with 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G. According to the present process 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be prepared in substantially pure form.

In order that the invention may be more fully understood the foregoing processes are exemplified below. These examples are illustrative and are not intended to limit the scope of the invention in any way.

EXAMPLE 1

1-(1-methyl-1H-pyrazol-4-yl)-N-((1R,5S,7S)-9-methyl-3-oxa-9-azabicyclo[3.3.1]nonan-7-yl)-1H-indole-3-carboxamide 1-(1-Methyl-1H-pyrazol-4-yl)-1H-indole-3-carboxylic acid (128.7 g, 0.53 mol) and anhydrous THF (645 mL) was heated to about 43° C. Oxalyl chloride (137.7 g, 92 mL, 1.08 mol) was added dropwise between 40 and 50° C. Gas evolution ceased in approximately 30 minutes. The resulting suspension was stirred for 2 hours at 50° C., allowed to cool to room temperature, and then stirred overnight. The suspension was diluted with heptane (1.5 L), stirred for 10 minutes, and allowed to settle. The supernatant was removed. The addition of heptane (1.5 L), followed by stirring, settling, and decanting was repeated two more times.

The resulting suspension was diluted with anhydrous THF (645 mL) and the ratio between THF and heptane was determined by NMR to be 3:2. The reaction mixture was cooled to 5° C. and to the mixture was added DIPEA base (138 g, 1.07 mol) at such a rate that the temperature did not exceed 20° C. Next (1R,5S,7S)-9-methyl-3-oxa-9-azabicyclo[3.3.1]nonan-7-amine (101.4 g, 0.63 mol) in 500 mL of anhydrous THF was added. The reaction mixture was warmed to ambient temperature and stirred at 20 to 23° C. overnight to give a suspension.

The suspension was filtered and the cake was dissolved in 1N HCl (2.6 L). The aqueous layer was washed with EtOAc (3×2.6 L). The aqueous layer was cooled to 5° C. and was basified to pH 12 with aqueous potassium hydroxide (230 g) solution in water (500 mL). The mixture was stirred at 5 to 10° C. overnight to give a solid. The product was filtered, washed with water (2×1.2 L), followed by MTBE (2×1.2 L), and then dried to give 128 g (64%) of the (crude) title compound.

EXAMPLE 2

1-(1-methyl-1H-pyrazol-4-yl)-N-((1R,5S,7S)-9-methyl-3-oxa-9-azabicyclo[3.3.1]nonan-7-yl)-1H-indole-3-carboxamide 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (17 g, 44.8 mmol) in EtOAc (500 mL) and 250 mL of HCl/EtOAc (4M) was added, and the mixture was stirred at room temperature for 30 minutes. The reaction mixture was then concentrated to dryness to give 1-(1-methyl-1H-pyrazol-4-yl)-N-((1R,5S,7s)-9-methyl-3-oxa-9-azabicyclo[3.3.1]nonan-7-yl)-1H-indole-3-carboxamide, bis-hydrogen chloride salt (18 g, 39.8 mmol, 89% yield).

1-(1-Methyl-1H-pyrazol-4-yl)-N-((1R,5S,7s)-9-methyl-3-oxa-9-azabicyclo[3.3.1]nonan-7-yl)-1H-indole-3-carboxamide, bis-hydrogen chloride salt was combined with DMSO (80 mL) and the mixture was heated in oil bath to 50° C. until a homogeneous solution was formed. An aqueous sodium hydroxide solution (4M, 9.28 mL, 37.1 mmol) was added via addition funnel over 3 minutes. After stirring for 5 minutes, water (80 mL) was added slowly via addition funnel over 10 minutes at 50° C. After the water addition was completed the internal temp was kept at 51° C. The reaction was stirred at 50° C. for 1 hour and then cooled to room temperature over 3 hour period to give a solid. The solid was collected by filtration, washed with water (24 mL), air dried for 1 hour, followed by vacuum oven drying at 50° C. overnight to give a hydrate of the title compound.

EXAMPLE 3

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7s)-9-methyl-3-oxa-9-azabicyclo[3.3.1]nonan-7-yl)-1H-indole-3-carboxamide (300 mg, 0.791 mmol) was combined with DMSO (2.1 mL) and was heated on reaction block to 80° C. with stirring. Water (3.90 mL) was added slowly via syringe in 3 portions over 15 minutes. The reaction was stirred at 80° C. for 30 minutes before slowly cooled to room temperature over 4 hours and stirred overnight at room temperature to give a solid. The solid was collected by filtration, washed with water (3×2 mL), air dried for 1 hour, followed by high vacuum drying at room temperature for 4 hours to give the title compound.

EXAMPLE 4

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (25.9 mg) and DMSO (0.4 mL) were combined and heated to 70° C. Water (0.6 mL) was added and the mixture was stored at 4° C. overnight. The solids were collected by centrifugation, dried in vacuo at ambient temperature to give the title compound.

EXAMPLE 5

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (25.9 mg) and DMSO (0.4 mL) were combined and heated to 70° C. Water (0.6 mL) was added and the mixture was cooled to ambient temperature at a rate of 20° C. per hour and allowed to equilibrate with stirring at ambient temperature over 16 hours. The solids were collected by centrifugation, dried in vacuo at ambient temperature to give the title compound.

EXAMPLE 6

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (31.0 mg) and MeOH (1.0 mL) were combined and heated to 60° C. MTBE (2.0 mL) was added and the mixture was stored at 4° C. overnight. The solids were collected by centrifugation, dried in vacuo at ambient temperature to give the title compound.

EXAMPLE 7

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (29.8 mg) and MeCN (1.0 mL) were combined and heated to 70° C. MTBE (2.0 mL) was added and the mixture was stored at 4° C. overnight. The solids were collected by centrifugation, dried in vacuo at ambient temperature to give the title compound.

EXAMPLE 8

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (30.6 mg) and THF (0.5 mL) were combined and heated to 70° C. MTBE (1.0 mL) was added and the mixture was stored at 4° C. overnight. The solids were collected by centrifugation, dried in vacuo at ambient temperature to give the title compound.

EXAMPLE 9

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (27.5 mg) and toluene (2.0 mL) were combined and heated to 70° C. MTBE (4.0 mL) was added and the mixture was stored at 4° C. overnight. The solids were collected by centrifugation, dried in vacuo at ambient temperature to give the title compound.

EXAMPLE 10

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (26.5 mg) and acetone (0.5 mL) were combined and heated to 60° C. MTBE (1.0 mL) was added and the mixture was stored at 4° C. overnight. The solids were collected by centrifugation, dried in vacuo at ambient temperature to give the title compound.

EXAMPLE 11

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (29.3 mg) and EtOH (0.5 mL) were combined and heated to 70° C. MTBE (1.0 mL) was added and the mixture was cooled to ambient temperature at a rate of 20° C. per hour and allowed to equilibrate with stirring at ambient temperature over 16 hours. The solids were collected by centrifugation, dried in vacuo at ambient temperature to give the title compound.

EXAMPLE 12

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (27.8 mg) and IPA (0.5 mL) were combined and heated to 70° C. MTBE (1.0 mL) was added and the mixture was cooled to ambient temperature at a rate of 20° C. per hour and allowed to equilibrate with stirring at ambient temperature over 16 hours. The solids were collected by centrifugation, dried in vacuo at ambient temperature to give the title compound.

EXAMPLE 13

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (31.4 mg) and acetone (0.5 mL) were combined and heated to 50° C. Heptane (1.0 mL) was added and the mixture was stored at 4° C. overnight. The solids were collected by centrifugation, dried in vacuo at ambient temperature to give the title compound.

EXAMPLE 14

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (34.5 mg) and EtOH (1.0 mL) were combined and heated to 70° C. Heptane (2.0 mL) was added and the mixture was cooled to ambient temperature at a rate of 20° C. per hour and allowed to equilibrate with stirring at ambient temperature over 16 hours. The solids were collected by centrifugation, dried in vacuo at ambient temperature to give the title compound.

EXAMPLE 15

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (58.3 mg) and IPA (1.0 mL) were combined and heated to 70° C. MTBE (2.0 mL) was added and the mixture was stored at 4° C. overnight. The solids were collected by centrifugation, dried in vacuo at ambient temperature to give the title compound.

EXAMPLE 16

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (61.5 mg) and acetone (1.0 mL) were combined and heated to 60° C. MTBE (1.5 mL) was added and the mixture was stored at 4° C. overnight. The solids were collected by centrifugation, dried in vacuo at ambient temperature to give the title compound.

EXAMPLE 17

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (27.4 mg) and IPA (1.0 mL) were combined and heated to 70° C. Water (1.5 mL) was added and the mixture was stored at 4° C. overnight. The solids were collected by centrifugation, dried in vacuo at ambient temperature to give the title compound.

EXAMPLE 18

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (24.3 mg) and NMP (1.0 mL) were combined and heated to 70° C. Water (0.6 mL) was added and the mixture was stored at 4° C. overnight. The solids were collected by centrifugation, dried in vacuo at ambient temperature to give the title compound.

EXAMPLE 19

1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G 1-(1-Methyl-1H-pyrazol-4-yl)-N-((1R,5S,7S)-9-methyl-3-oxa-9-azabicyclo[3.3.1]nonan-7-yl)-1H-indole-3-carboxamide (126 g) was dissolved in a mixture of denatured ethanol, containing 5% methanol and 5% isopropanol (1070 mL), and DMSO (1070 mL) at 70° C. and stirred for 1 hour. The resulting solution was filtered through a paper filter, reheated to 70° C., and then cooled to 50° C. over 30 minutes. Seeds of Form G (1.3 g) were added. The temperature was raised to 70° C., and then cooled to 50° C. over 30 minutes. Seeds of Form G (1.3 g) were again added and the resulting suspension was cooled to 40° C. over 30 minutes and kept at this temperature with stirring for 5 hours. The resulting suspension was then cooled to 5° C. over 1 hour and was stirred at this temperature for 6 hours. The resulting solid was collected by filtration, washed with ethanol (2×250 mL), and dried under vacuum over 3 days at 40° C. to give the title compound.

1-(1-Methyl-1H-pyrazol-4-yl)-N-((1R,5S,7S)-9-methyl-3-oxa-9-azabicyclo[3.3.1]nonan-7-yl)-1H-indole-3-carboxamide, Form G, is a 5-HT3 inhibitor. Receptors of 5-HT3 are known to be expressed in the central nervous system in regions involving vomiting reflex, processing of pain, cognition and anxiety control and play a role in the pathogenesis of diseases such as emesis, migraine, drug addiction, and neurodegenerative and psychiatric disorders such as anxiety and depression (see Hewlett et al., 2003 J. Clin. Psychiatry 64, 1025-1030; Kelley et al., 2003a, Eur J. Pharmacol., 461, 19-25; Haus et al., 2000 Scand J Rheumatol Suppl 113, 55-58; and Faris et al., 2006 J affect Disorder 92, 79-90), eating disorders (Hammer et al., 1990 Am J Physiol 259, R627-R636, and Jiang & Gietzen 1994 Pharmacol Biochem Behav 47, 59-63), schizophrenia (see Hermann et al. 1996 Biochem Biophys Res Commun 225, 957-960; Sirota et al., 2000 Am J Psychiatry 157, 287-289; Adler et al., 2005 Am J Psychiatry 162, 386-388; Koike et al., Levkovitz et al, 2005 Schizophr Res 76, 67-72), cognitive dysfunction associated with schizophrenia (see Zhang et al., 2006 Schizophr Res 88, 102-110; Akhondzadeh et al., 2009 Schizophr Res 107, 206-212), cognitive dysfunction associated with Parkinson's disease, Huntington's Chorea, presenile dementias and Alzheimer's disease (see Costall and Naylor 2004 CNS Neurol Disord 3, 27-37) substance abuse and addiction (see Johnson et al., 2002 Psycho-pharmacology (Berl) 160, 408-413; Johnson, 2004 CNS Drugs 18, 1105-1118; Dawes et al., 2005 Addict Behav 30, 1630-1637, Johnson 2006 Drug Alcohol Depend 84, 256-263), and pain (see Kayser et al, 2007 Pain 130, 235; Glaum et al., 1998 Neurosci Lett 95, 313-317; Schworer & Ramadori 1993 Clin Investig 71, 659; Thompson and Lummis 2007 Exp Opin Ther Targets, 11, 527-540). In addition, 5-HT3 receptors are expressed in the GI tract and hence may play a role in GI disorders such as dyspepsia, gastroesophagal reflux disease and irritable bowel syndrome (see Graeff 1997 Psychiatr Clin North Am 20, 723; Thompson and Lummis 2007 Exp Opin Ther Targets, 11, 527-540; Barnes et al. 2009 Neuropharmacology 56, 273). Expression of the 5-HT3A subunit has also been discovered extraneuronally in immune cells such as monocytes, chondrocytes, T-cells, synovial tissue and platelets (Fiebich et al., 2004 Scan J Rheumatol Suppl, 9-11, Stratz et al., 2008 Thromb Haemost 99, 784) and of 5-HT3A, C-E within the lamina propia in the epithelium of the gut mucosa (Kapeller et al., J Comp Neuro, 2008; 509: 356-371) thus suggesting they may be involved in immunological and inflammatory diseases like atherosclerosis, tendomyopathies and fibromyalgia.

The 5-HT3 inhibitory activity of 1-(1-methyl-1H-pyrazol-4-yl)-N-((1R,5S,7S)-9-methyl-3-oxa-9-azabicyclo[3.3.1] nonan-7-yl)-1H-indole-3-carboxamide, Form G, may be tested using the in vitro assay and in vivo assay described in PCT Publication No. WO 2014/014951, published Jan. 23, 2014.

In general, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, will be administered in a therapeutically effective amount by any of the accepted modes of administration for agents that serve similar utilities. Therapeutically effective amounts of 1-(1-methyl-1H-pyrazol-4-yl)-N-((1R,5S,7S)-9-methyl-3-oxa-9-azabicyclo[3.3.1] nonan-7-yl)-1H-indole-3-carboxamide, Form G, may range from about 0.01 to about 75 mg per kg patient body weight per day, which can be administered in single or multiple doses. Preferably, the dosage level will be about 0.01 to about 10 mg/kg per day; more preferably about 0.5 to about 5 mg/kg per day or 0.1-2 mg/kg/day. For oral administration, the compositions are preferably provided in the form of tablets containing about 0.5 to about 200 milligrams of the active ingredient, from about 0.5, 1.0, 5.0, 10, 15, 20, 25, 50, 75, 100, 150, or 200 milligrams of the active ingredient. The actual amount of 1-(1-methyl-1H-pyrazol-4-yl)-N-((1R,5S, 7S)-9-methyl-3-oxa-9-azabicyclo[3.3.1]nonan-7-yl)-1H-indole-3-carboxamide, Form G, i.e., the active ingredient, will depend upon numerous factors such as the severity of the disease to be treated, the age and relative health of the subject, the route and form of administration, and other factors. Although these dosages are based on an average human subject having a mass of about 60 kg to about 70 kg, the physician will be able to determine the appropriate dose for a patient (e.g., an infant) whose mass falls outside of this weight range.

In general, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral dosing using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, in combination with at least one pharmaceutically acceptable excipient. Acceptable excipients are non-toxic, aid administration, and do not adversely affect the therapeutic benefit of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The level of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, in a formulation can vary within the full range employed by those skilled in the art. Typically, the formulation will contain, on a weight percent (wt %) basis, from about 0.01-99.99 wt % of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, based on the total formulation, with the balance being one or more suitable pharmaceutical excipients. Preferably, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, is present at a level of about 1-80 wt %.

1-(1-Methyl-1H-pyrazol-4-yl)-N-((1R,5S,7S)-9-methyl-3-oxa-9-azabicyclo[3.3.1]nonan-7-yl)-1H-indole-3-carboxamide, Form G, may be used in combination with one or more other drugs in the treatment of diseases or conditions for which 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, or the other drugs may have utility, where the combination of the drugs together are safer or more effective than either drug alone. Such other drug(s) may be administered, by a route and in an amount commonly used therefore, contemporaneously or sequentially with 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G. When 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, is used contemporaneously with one or more other drugs, a pharmaceutical composition in unit dosage form containing such other drugs and 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be used. However, the combination therapy may also include therapies in which 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, and one or more other drugs are administered on different overlapping schedules. It is also contemplated that when used in combination with one or more other active ingredients, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, and the other active ingredients may be used in lower doses than when each is used singly.

Accordingly, the pharmaceutical compositions of the present invention also include those that contain one or more other active ingredients, in addition to 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G.

The above combinations include combinations of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, not only with one other active compound, but also with two or more other active compounds. Likewise, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be used in combination with other drugs that are used in the prevention, treatment, control, amelioration, or reduction of risk of the diseases or conditions for which 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, are useful. Such other drugs may be administered, by a route and in an amount commonly used therefore, contemporaneously or sequentially with 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G. Accordingly, the pharmaceutical compositions of the present invention also include those that also contain one or more other active ingredients, in addition to 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G. The weight ratio of the 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, to the second active ingredient may be varied and will depend upon the effective dose of each ingredient. Generally, an effective dose of each will be used.

In one embodiment, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be administered in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be administered in combination with sedatives, hypnotics, anxiolytics, antipsychotics, anti-anxiety agents, cyclopyrrolones, imidazopyridines, pyrazolopyrimidines, minor tranquilizers, melatonin agonists and antagonists, melatonergic agents, benzodiazepines, barbiturates, mGlu2/3 agonists, 5HT-2 antagonists, PDE10 antagonists, GlyT1 inhibitors, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazopam, lormetazepam, maprotiline, mecloqualone, melatonin, mephobarbital, meprobamate, methaqualone, midaflur, midazolam, nefazodone, nisobamate, nitrazopam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazopam, thioridazine, thiothixene, tracazolate, kanylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, [4-(3-fluoro-5-trifluoromethylpyridin-2-yl)piperazin-1-yl][5-methanesulfonyl-2-((S)-2,2,2-trifluoro-1-methylethoxy)phenyl]methanone (RG1678), glyt1 inhibitors disclosed in U.S. Pat. No. 7,538,114, Table 1 in column 14, and salts thereof, and combinations thereof.

In another embodiment, 1-(1-methyl-1H-pyrazol-4-yl)-N-((1R,5S,7S)-9-methyl-3-oxa-9-azabicyclo[3.3.1]nonan- 7-yl)-1H-indole-3-carboxamide, Form G, may be administered in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and prarnipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be administered in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be administered in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, 1-(1-methyl-1H-pyrazol-4-yl)-N-((1R,5S,7S)-9-methyl-3-oxa-9-azabicyclo[3.3.1]nonan-7-yl)-1H-indole-3-carboxamide, Form G, may be administered in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, adrenoreceptor antagonists, neurokinin-1 receptor antagonists, atypical anti-depressants, benzodiazopines, 5-HTA agonists or antagonists, especially 5-HTA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide, venlafaxine; duloxetine; aprepitant; bupropion, lithium, nefazodone, trazodone and viloxazine; alprazolam, chlordiazepoxide, clonazopam, chlorazepate, diazopam, halazepam, lorazepam, oxazopam and prazepam; buspirone, flesinoxan, gepirone and ipsapirone, and pharmaceutically acceptable salts thereof.

What is claimed is:

1. A crystalline form of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, free base, which is characterized by a powder X-ray diffraction pattern obtained using a copper X-ray source, the powder X-ray diffraction pattern comprising peaks at 8.13±0.2 degrees 2-theta and 18.39±0.2 degrees 2-theta and the powder X-ray diffraction pattern further comprising one or more peaks selected from 17.01±0.2 degrees 2-theta, 17.49±0.2 degrees 2-theta, and 20.91±0.2 degrees 2-theta.

2. The crystalline form according to claim 1, the powder X-ray diffraction pattern further comprising two or more peaks selected from 17.01±0.2 degrees 2-theta, 17.49±0.2 degrees 2-theta, and 20.91±0.2 degrees 2-theta.

3. The crystalline form according to claim 2, the powder X-ray diffraction pattern comprising peaks at 8.13±0.2 degrees 2-theta, 17.01±0.2 degrees 2-theta, 17.49±0.2 degrees 2-theta, 18.39±0.2 degrees 2-theta, and 20.91±0.2 degrees 2-theta.

4. A pharmaceutical composition comprising a crystalline form of 1-(1-methyl-1H-pyrazol-4-yl)-N-((1R,5S,7S)-9-methyl-3-oxa-9-azabicyclo[3.3.1]nonan-7-yl)-1H-indole-3-carboxamide as defined in claim 1, and a pharmaceutically acceptable excipient.

5. A method for treating a disease in a subject, the method comprising administering to the subject a crystalline form of 1-(1-methyl-1H-pyrazol-4-yl)-N-((1R,5S,7S)-9-methyl-3-oxa-9-azabicyclo[3.3.1]nonan-7-yl)-1H-indole-3-carboxamide as defined in claim 1, at a dose within a range of about 0.01 to about 10 mg/kg per day, wherein the disease is selected from emesis, migraine, substance abuse, substance addiction, anxiety, depression, eating disorder, schizophrenia, cognitive dysfunction associated with schizophrenia, Parkinson's disease, Huntington's Chorea, presenile dementia, Alzheimer's disease, pain, dyspepsia, gastroesophagal gastroesophageal reflux disease, irritable bowel syndrome, atherosclerosis, tendomyopathies and fibromyalgia.

6. The method according to claim 5, wherein the disease is cognitive dysfunction associated with schizophrenia.

* * * * *